United States Patent [19]

Nakamura et al.

[11] Patent Number: 4,848,356
[45] Date of Patent: Jul. 18, 1989

[54] ULTRASONIC DOPPLER BLOOD FLOWMETER

[75] Inventors: Yasuhiro Nakamura, Tokyo; Masami Kawabuchi, Yokohama, both of Japan

[73] Assignee: Matsushita Electrical Industrial Co., Ltd., Osaka, Japan

[21] Appl. No.: 253,024

[22] Filed: Oct. 4, 1988

Related U.S. Application Data

[62] Division of Ser. No. 865,012, May 20, 1986.

[30] Foreign Application Priority Data

May 20, 1985 [JP] Japan .............................. 60-107354
Dec. 27, 1985 [JP] Japan .............................. 60-296790

[51] Int. Cl.⁴ .............................................. A61B 8/06
[52] U.S. Cl. .............................................. 128/661.07
[58] Field of Search ............... 73/861.25; 128/661.07, 128/661.09, 691

[56] References Cited

U.S. PATENT DOCUMENTS

| | | | |
|---|---|---|---|
| 3,763,851 | 10/1973 | Haff et al. ...................... | 128/661.07 |
| 3,934,577 | 1/1976 | Romani .......................... | 128/661.07 |
| 3,991,365 | 11/1976 | Takeuchi ........................ | 128/661.07 |
| 4,357,944 | 11/1982 | Mauser et al. .................. | 128/661.07 |
| 4,541,437 | 9/1985 | Amemiya ........................ | 128/661.09 |
| 4,583,409 | 4/1986 | Lannuzel et al. .............. | 128/660.02 |
| 4,612,937 | 9/1986 | Miller ............................. | 128/660.05 |
| 4,660,565 | 4/1987 | Shirasaka ....................... | 128/661.09 |
| 4,680,739 | 7/1987 | Lannuzel ........................ | 128/661.09 |
| 4,693,319 | 9/1987 | Amemiya ........................ | 73/861.25 |

Primary Examiner—Francis Jaworski
Assistant Examiner—George Manuel
Attorney, Agent, or Firm—Wenderoth, Lind & Ponack

[57] ABSTRACT

An ultrasonic Doppler blood flowmeter measures the velocity of blood flow at an arbitrary position of the body of a subject by making use of Doppler shift of an ultrasonic echo signal. The echo signal including Doppler shift from the blood flow of the body is detected in phase on the basis of standard reference signal, and the distance to an intended position is extracted from the phase detected signal and is integrated, and the direct-current component or ultraflow frequency component of the Doppler shift signal obtained from the integrator means is fed back negatively to the integrator means. As a result, the echo signal components of the body tissues are removed, and the frequency of blood flow only can be analyzed, so that an accurate blood flow information may be obtained.

7 Claims, 10 Drawing Sheets

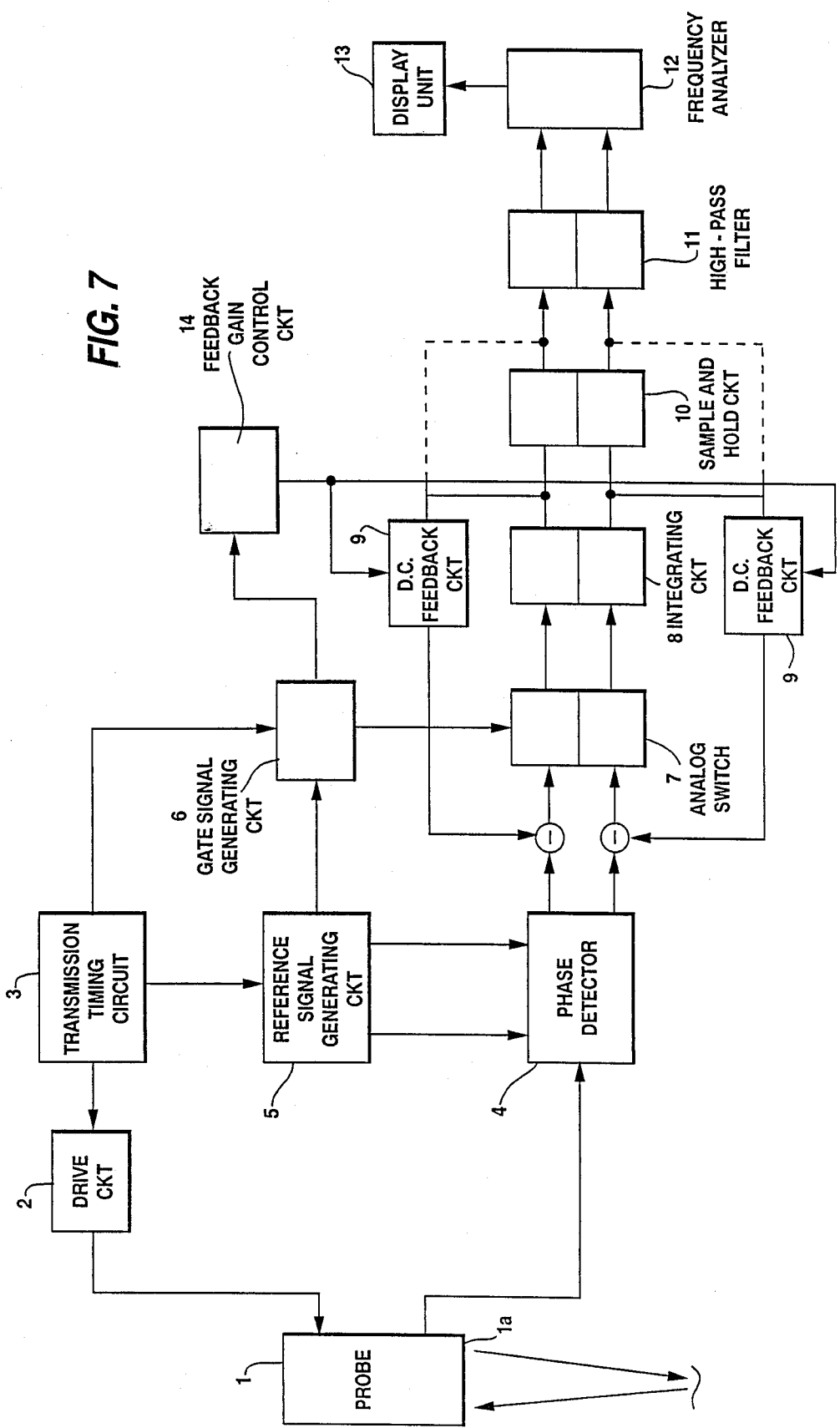

ULTRASONIC DOPPLER BLOOD FLOWMETER

This application is a divisional of application Ser. No. 865,012, filed 5/20/86.

BACKGROUND OF THE INVENTION

This invention relates to an ultrasonic Doppler blood flowmeter used in the measurement of the velocity of blood flow at an arbitrary position within the body of a subject in the medical field.

DESCRIPTION OF THE PRIOR ART

Recently, ultrasonic Doppler blood flowmeters have been used in the medical field for use in the cardiovascular system. Its operation depends on the principle that the ultrasonic wave transmitted into the body undergoes a frequency shift due to the Doppler effect which occurs when the wave is reflected by a moving substance such as blood flow, and by indicating the Doppler shift frequency corresponding to the rate of blood flow, the distribution of the rate of blood flow in the body can be easily observed from the surface of the body. Such an ultrasonic Doppler blood flowmeter is disclosed, for example, in IEEE, Trans. S.U., SU-17 (3), p.170, 1970.

Referring now to FIG. 1, the conventional ultrasonic Doppler blood flowmeter is described below. In this diagram, numeral 101 denotes an ultrasonic transmission and reception means (probe) which transmits ultrasonic pulses into the body from an ultrasonic transmission/reception plane 101a, and receives an echo signal which is reflected due to the difference in the acoustic impedances, generally the probe 101 is made of a piezoelectric material. Numeral 102 is a drive circuit which generates the drive voltage for generating ultrasonic pulses to be transmitted from the probe 101 at the timing of an external trigger and at the frequency of an external clock; the drive circuit 102 drives the probe 101 element; 103 is a transmission timing circuit which provides the timing for the drive circuit 102 to generate a drive voltage used as a trigger; element 104 is a phase detector used to detect the phase of the echo signal received by the probe 101; element 105 is a reference signal generating circuit to serve as the reference of the frequency and phase of reference signal when detecting the phase of the transmission signal and echo signal of the drive circuit 102 by means of the phase detector 104; element 106 is a gate signal generating circuit which generates a gate signal at the timing corresponding to the propagation time of the ultrasonic wave up to the transmission/reception plane of the probe 101 and the desired position; element 107 is an analog switch which causes the phase signal detected by the phase detector 104 to pass during the interval of the gate signal generated by the gate signal generating circuit 106; element 108 is an integrating circuit which integrates the phase signal passing through the analog switch 107, and thereby determines the sum of phase signals, and repeats the transmission and reception to obtain a Doppler shift signal; element 110 is a sample and hold circuit which holds the integrated result for resetting until the result of next integration is obtained prior to integration by the integrating circuit 108; element 111 is a high pass filter which removes signals of less than several hundred hertz from the Doppler shift signal obtained in the integrating circuit 108; element 112 is a frequency analyzer which analyzes the frequency of the Doppler shift signal passing through the high pass filter 111; and element 113 is a display unit which indicates the result of frequency analyzer 112.

While referring to the time chart shown in FIG. 2, its action is described below. In the transmission timing circuit 103, trigger signals T of constant or arbitrary intervals are generated (a), and are supplied to the drive circuit 102. The drive circuit 102 drives the probe 101 by the trigger signals T in drive pulse TX (b), and the ultrasonic pulses are transmitted from this probe 101 into the body. The ultrasonic pulses propagate within the body, and are reflected by the parts differing in their acoustic impedance, and return to the probe 101, being received as echo signals E (c). The echo signals E are obtained at a delay time $t_d$ from $t_o$ of trigger signal T, corresponding to the reciprocal propagation time of the ultrasonic wave from the transmission/reception plane 101a of the probe 101 to the reflecting point of the transmitted ultrasonic pulse, and since the echo signals from a moving reflecting body always vary in the reciprocal propagation time, $t_d$ also changes. Assuming that the variation of propagation time changing within the period of trigger signal T to be $\Delta t_d$ and the echo signal intensity to be A, then the echo signal E obtained by the n-th transmission/reception is expressed by the following equation.

$$E = A \cos\{\omega(t_d + n\cdot\Delta t_d)\} \tag{1}$$

This is orthogonally detected, using the reference signal R (d) as mentioned below by the phase detector 104. The reference signal is available, though not shown, as $V_X$ and $V_Y$ which are uniform in amplitude but mutually different in phase by 90° from time $t_o$ of trigger signal T, which are expressed as follows.

$$V_X = \cos\omega t_d \tag{2}$$

$$V_Y = \sin\omega t_d$$

By the phase detector 104, the following signals are obtained by multiplying $V_X$, $V_Y$ of eq. (2) by E of eq. (1).

$$E \cdot V_X = (A/2) \cdot \{\cos(\omega n \Delta t_d) + \sin(2\omega t + \omega n \Delta t_d)\} \tag{3}$$

$$E \cdot V_Y = (A/2) \cdot \{\sin(2\omega t + \omega n \Delta t_d) - \sin(\omega n \Delta t_d)\}$$

Two signals C (e) of eq. (3) obtained in the phase detector 104 are integrated in the integrating circuit 108 by turning on the analog switch 107 in the period of $t_1$ to $t_2$ of gate signal G (f) generated by the gate signal generating circuit 106. The signal C (e) expressed in eq. (3) is composed of two signal components ($\omega n \Delta t_d$) and ($2\omega t + \omega n \Delta t_d$), and the former does not contain the parameter t of time and is a direct-current signal, while the latter is a high frequency signal with a frequency which is twice as high as the transmission frequency $\omega$. Therefore, by passing through the integrating circuit 108, the latter component is eliminated, and the Doppler shift signals X Y obtained as a result at the integration end time $t_2$ are as follows.

$$X = (A/2) \cdot K \cdot t_G \cdot \cos(\omega n \Delta t_d) \tag{4}$$

$$Y = -(A/2) \cdot K \cdot t_G \cdot \sin(\omega n \Delta t_d) \tag{4}$$

where K is a constant determined by the circuit constant of the integrating circuit 108, and $t_G$ is a time width of the gate signal G. The gate signal G is intended to match with the time $t_1$ to $t_2$ when the echo signal from a desired position of the body is received, and the integration results X Y received the n-th time contain all of the echo signal information between $t_1$ and $t_2$ (g). The voltages of integration results X Y are held by the next sample and hold circuits 110 as indicated by the broken line (h) until the next n+1 time integration result is obtained. The integrating circuit 108 is reset when holding of the sample at hold circuits 110 is over.

Thus, the obtained integration result is a direct-current voltage, as clear from eq. (4), when transmitted and received only once, but since the transmission and reception are repeated every period T of the trigger signal, n increases, and X Y continue to change while keeping a phase difference of 90°. This is an orthogonal Doppler signal, if, for example, X is a real part signal and Y is an imaginary part signal. Both X and Y are obtained as discrete information at every period T, and the following relationship is established between the delay time amount $\Delta t_d$ varying in interval T from the n-th time transmission/reception and n+1 time transmission/reception.

$$\Delta t_d = (2vT)/C \qquad (5)$$

Therefore, from eqs. (4) and (5), the deviation frequency $f_d$ of Doppler shift signals X and Y is expressed as follows.

$$f_d = (2 \cdot v \cdot f \cdot \cos\theta)/C \qquad (6)$$

where C is the speed of sound propagation in the body, f is the reference signal frequency (which is generally equal to the transmitted ultrasonic pulse frequency), and $\theta$ is the angle formed by the moving direction of the reflecting substance and ultrasonic wave running direction. In the body, when an echo signal from blood flow is captured, since the intensity of reflection by the blood flow is very small, the amplitude of Doppler shift signal is extremely weak, while the rate of blood flow is fast, so that the deviation frequency $f_d$ becomes high. In the body tissues such as viscera, the intensity of reflection A is high, and the movement is slow by the internal body movement or the like, and the deviation frequency $f_d$ is very low. By passing it through the high pass filter 111, only the Doppler shift signal from the blood flow having a small amplitude and high frequency can be obtained. To remove the Doppler shift signal from the body tissues is very important for expanding the dynamic range of the frequency analyzer 112, and it is generally set at 100 to 1 kHz. In the frequency analyzer 112, the Doppler shift signals X and Y are analyzed in frequency, and the direction of the blood flow is determined from the phase relationship of the two signals, and is displayed in the display unit 112 as a blood flow pattern.

However, as compared with trigger signal T shown in FIG. 3(a), the echo signal E is roughly divided into the very intense portion b from the body tissues appearing to be nearly standstill as shown in FIG. 3(b), and the feeble portion a from the blood flow which is always moving. To measure the rate of blood flow, it is necessary to amplify the feeble echo signal portion a from the blood flow with a large gain, and with the feeble echo signal from the blood flow alone, the real part signal Xa and imaginary part signal Ya having only alternating-current components are obtained in the integrating circuit 108 in the amplitude of up to amplitude limit V of the integrating circuit (c). When the setting of the measuring point is at the intense echo signal portion b from the body tissue, the phase difference of reference signal R and echo signal E is always constant or changes very slowly, and at the output of the integrating circuit 108, the direct-current component or the alternating-current component of the real part signal Xb and the imaginary part signal Yb with a very slow change appears (d). In the actual clinical application, since the ultrasonic beam transmitted from the probe 101 has a spread, if a blood vessel smaller in diameter than the beam diameter is captured, echo signals from the blood flow and body tissue may often exist at the same time, and conventionally, the effect of the body tissue was eliminated by using a high pass filter 111. However, when a relatively shallow measuring point is observed, for instance, the real part signal Xa and imaginary part signal Ya are superposed on the real part signal Xb and imaginary part signal Yb, resulting in Xc and Yc (e). But because of the amplitude limit V of the integrating circuit 108, the portion indicated by shaded area clips, and the waveform is distorted. When the direct-current component is small and saturation is not caused, it is possible to remove the direct-current component by the conventional high pass filter 111, but when measuring the blood flow in relatively superficial carotid artery or deep-seated fine blood vessels, the echo signal from the body tissue around the blood vessel is particularly intense due to spread of the ultrasonic beam, and the direct-current component increases particularly. As a result, the integrating circuit 108 is saturated by this direct-current component alone, and Doppler shift signal does not appear. Therefore, if the direct-current component is removed by the high pass filter 111, a Doppler shift signal cannot be obtained, and the result of frequency analysis involves unnecessary frequency components, or the result of analysis is suspended. Or, if either Doppler shift signal X or Y is saturated, information about the direction of blood flow cannot be obtained, which was a serious problem clinically.

The change of time $t_G$ while gate signal G is ON influences the shut-off frequency fc, and the low frequency component decreases as the gate width is wider, so that the obtained blood flow information varies depending on the gate width even at the same location. Generally, the frequency of the high pass filter 111 is set by the physician before use depending on the diagnostic condition, and the set frequency is shown on the operation panel or display unit of the apparatus, but the shut-off frequency fc of the integrating circuit affects the shut-off frequency of the high pass filter, and the displayed set frequency is no longer correct. Thus, depending on the gate width, the obtained information differs, and the displayed set frequency is not correct, and the accuracy as diagnostic data is lowered, and the reproducibility is inferior, and the result of diagnosis may differ depending on the gate width, which posed serious problems.

SUMMARY OF THE INVENTION

This invention is to solve the above-discussed problems of the prior art, and it is hence a primary object of this invention to present an ultrasonic Doppler blood flowmeter capable of analyzing the frequency of the blood flow only and obtaining an accurate blood flow information, by removing the direct-current components generated by the echo signals of body tissues from the real part output and imaginary part output delivered from the integrating circuit.

It is another object of this invention to present an ultrasonic Doppler blood flowmeter which is capable of diagnosing accurately by using the blood flow information and high pass filter characteristics and which is completely free from effects of the gate width.

These and other objects of this invention may be achieved by an apparatus which comprises a phase detector for detecting the phase of echo signals including Doppler shift from the blood flow in the body of a subject, a reference signal generating circuit to serve as the reference for the frequency and phase of the reference signal when detecting the phase of transmission signal from a drive circuit which drives an ultrasonic probe and the above echo signals, a gate signal generating circuit for generating a gate signal at the timing corresponding to the echo signal from an intended portion, a means for controlling the opening and closing of the phase signal detected by said phase detector by said gate signal, an integrating circuit for obtaining a Doppler shift signal by repeating transmission and reception by integrating the phase signal passing through said control means in the period of the above gate signal alone and determining the sum of the phases within the period of gate signal, and a direct-current feedback circuit which negatively feeds back the direct-current component or ultralow frequency component of the Doppler shift signal obtained in said integrating circuit into this integrating circuit.

BRIEF DESCRIPTION OF THE DRAWINGS

FIG. 7 is a block circuit diagram showing an ultrasonic Doppler blood flowmeter in a different embodiment of this invention;

FIG. 8(a) is a frequency characteristic diagram of the direct-current feedback circuit and FIG. 8(b) is a frequency characteristic diagram of the integrating circuit with negative feedback applied;

DETAILED DESCRIPTION OF THE INVENTION

Figure 4:
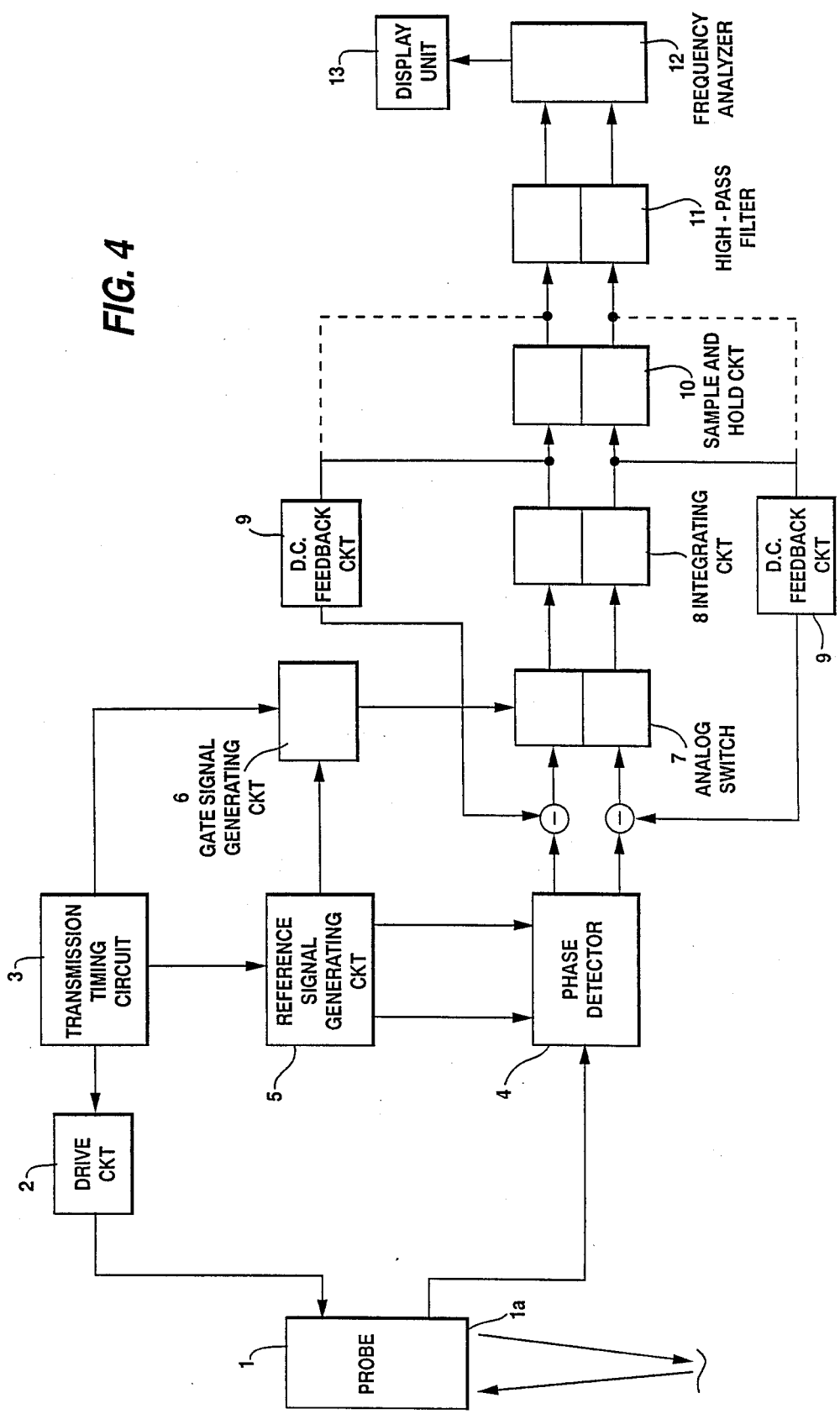
FIG. 4 is a block diagram representing one of the embodiments of an ultrasonic Doppler blood flowmeter according to this invention.

FIG. 4 is a block diagram of an ultrasonic Doppler blood flowmeter in one of the embodiments of this invention. The ultrasonic Doppler blood flowmeter of this invention possesses a direct-current current feedback circuit 9 for negatively feeding back the direct-current and ultraslow frequency components of the orthogonal signal delivered by the integrating circuit or sample and hold circuit in the above conventional ultrasonic Doppler blood flowmeter into the input of the integrating circuit of way of an analog switch.

That is, numeral 1 is an ultrasonic transmission and reception means (hereinafter called a probe) which transmits an ultrasonic pulse into the body from its ultrasonic transmission/reception plane 1a, and receives the echo signal reflected due to difference in the acoustic impedance. The probe 1 is generally made of a piezoelectric material. The probe 1 may be either a transmission/reception combination type or transmission and reception separate type. Numeral 2 denotes a drive circuit which drives the probe 1 by generating the drive voltage for generating ultrasonic pulses transmitted from the probe 1 at the frequency of an external clock and at a timing of an external trigger. Numeral 3 denotes a transmission timing circuit which provides the timing for the drive circuit 2 to generate the drive voltage as a trigger. Numeral 4 denotes a phase detector which detects the phase of echo signals received by the probe 1. Numeral 5 denotes a reference signal generating circuit which serves as the reference for frequency and phase of the reference signal when detecting the phase of the transmission signal and echo signal of the drive circuit 2 by means of the phase detector. Numeral 6 denotes a gate signal generating circuit which generates a gate signal at a time corresponding to the propagation time of the ultrasonic wave up to the transmission/reception plane 1a of the probe 1 and an intended position. Numeral 7 denotes an analog switch which causes the phase signal and direct-current feedback voltage detected by the phase detector 4 to pass through during the period of the gate signal generated by the gate signal generating circuit 6. Numeral 8 denotes an integrating circuit which integrates the phase signal passing through the analog switch 7, determines the sum of phase signals, repeats transmission and reception, and obtains Doppler shift signals. Numeral 10 denotes a sample and hold circuit which holds the integrated result for resetting until the next integration result is obtained prior to integration by the integrating circuit 8. Numeral 9 denotes a direct-current feedback circuit which negatively feeds back the direct-current component or ultralow frequency component of Doppler shift signal delivered from the integrating circuit 8 or sample and hold circuit 10 to the integrating circuit 8 by way of the analog switch 7. Numeral 11 denotes a high pass filter which removes signals of less than several hundred hertz from the Doppler shift signal obtained in the integrating circuit 8. Numeral 12 denoted a frequency analyzer which analyzes the frequency of the Doppler shift signal passing through the high pass filter 11. Numeral 13 denotes a display unit which shows the result of the frequency analyzer 12.

Figure 1:
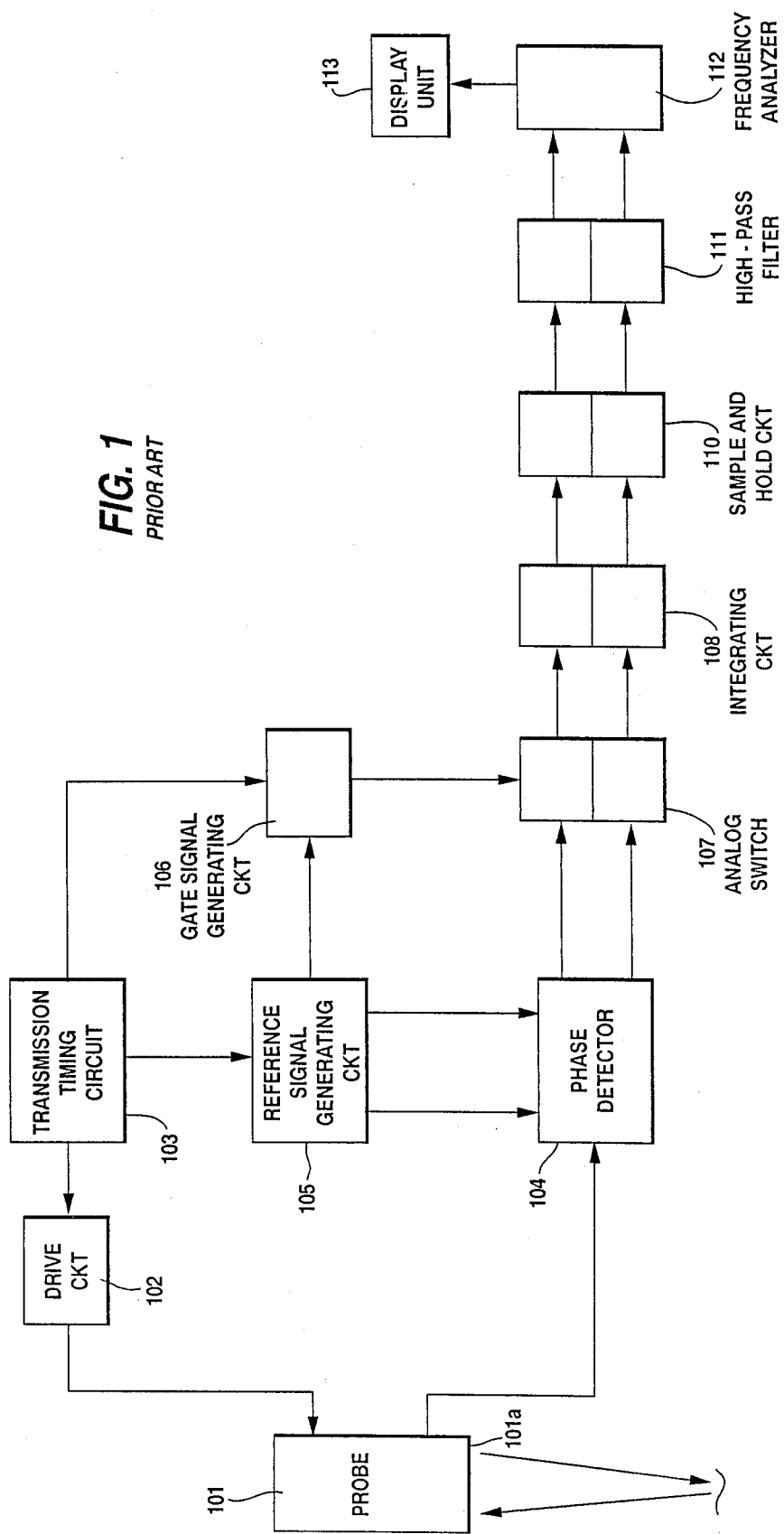
FIG. 1 is a block circuit diagram showing a conventional Doppler blood flowmeter.
Figure 2:
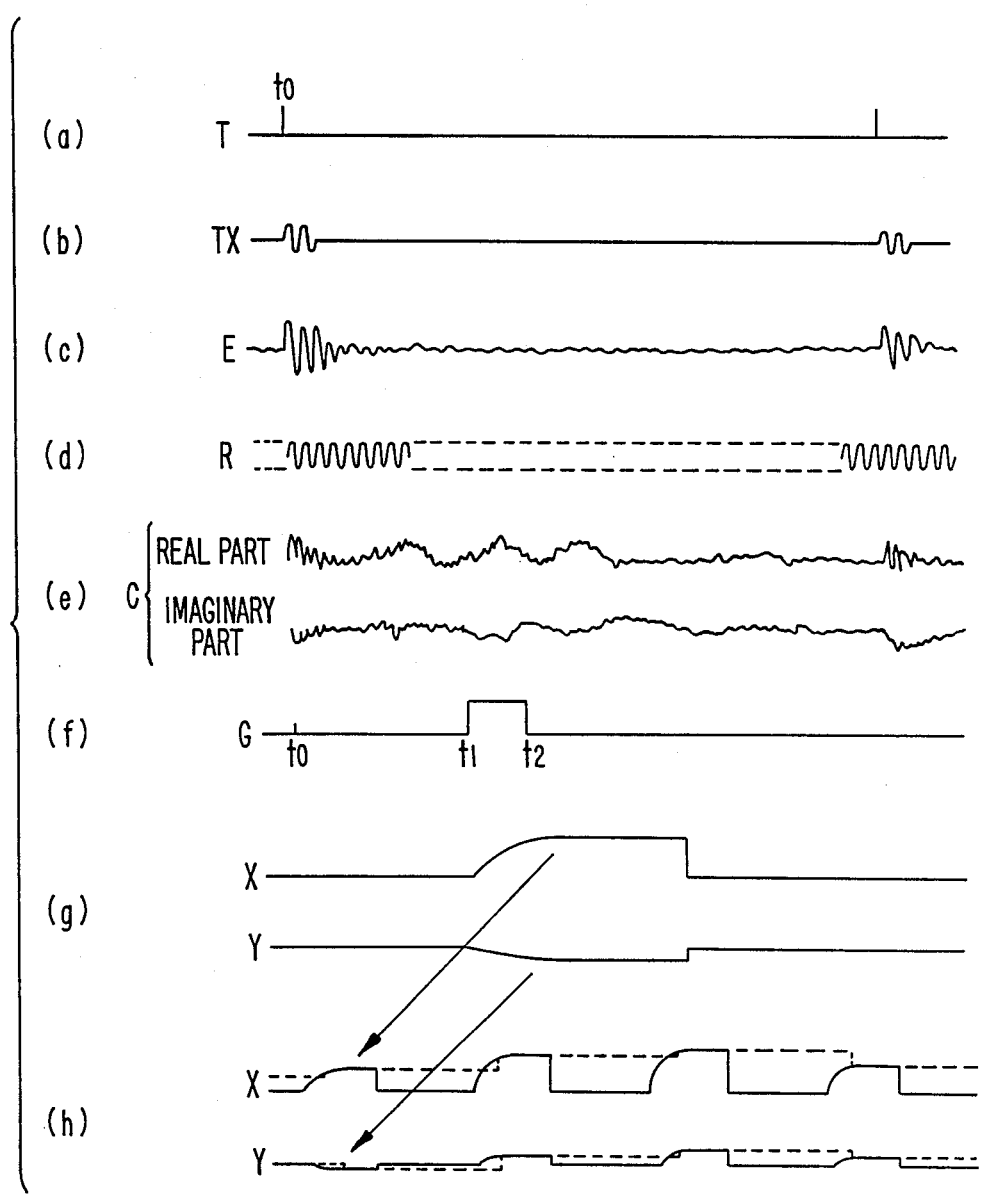
FIG. 2 is a time chart showing the operation of the flowmeter of FIG. 1.
Figure 3:
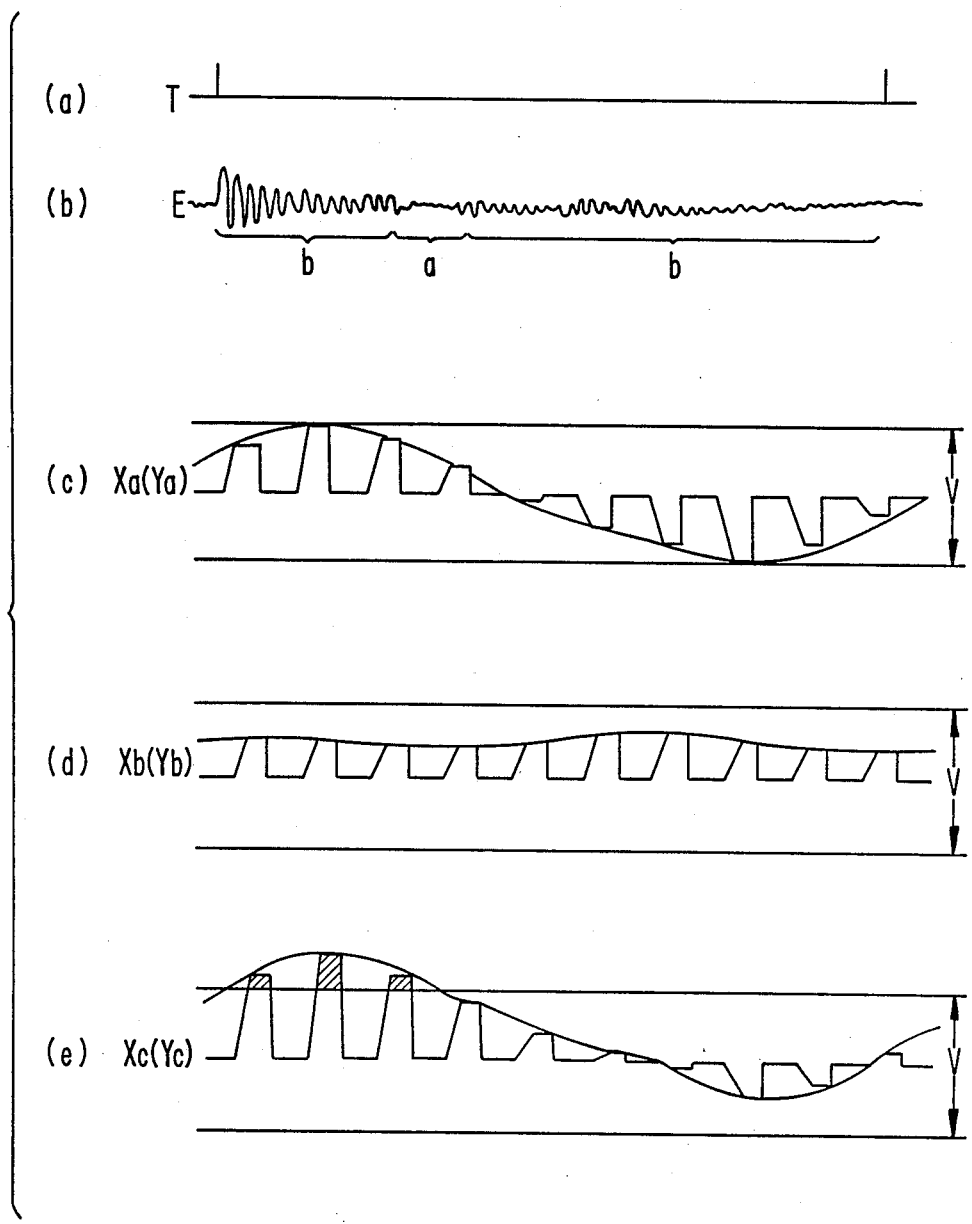
FIG. 3 is an integrated waveform obtained by using the flowmeter of FIG. 1.

The operation of this embodiment is described below. In this embodiment, too, the echo signal is orthogonally detected according to the route explained in the conventional example in FIGS. 1 and 2, and is displayed after frequency analysis. Here, the integrating circuit 8 outputs are negatively fed back by the direct-current components of the real part signal X and the imaginary part signal Y after integration, and it works as high pass filter in ultralow frequency region.

Figure 5A:
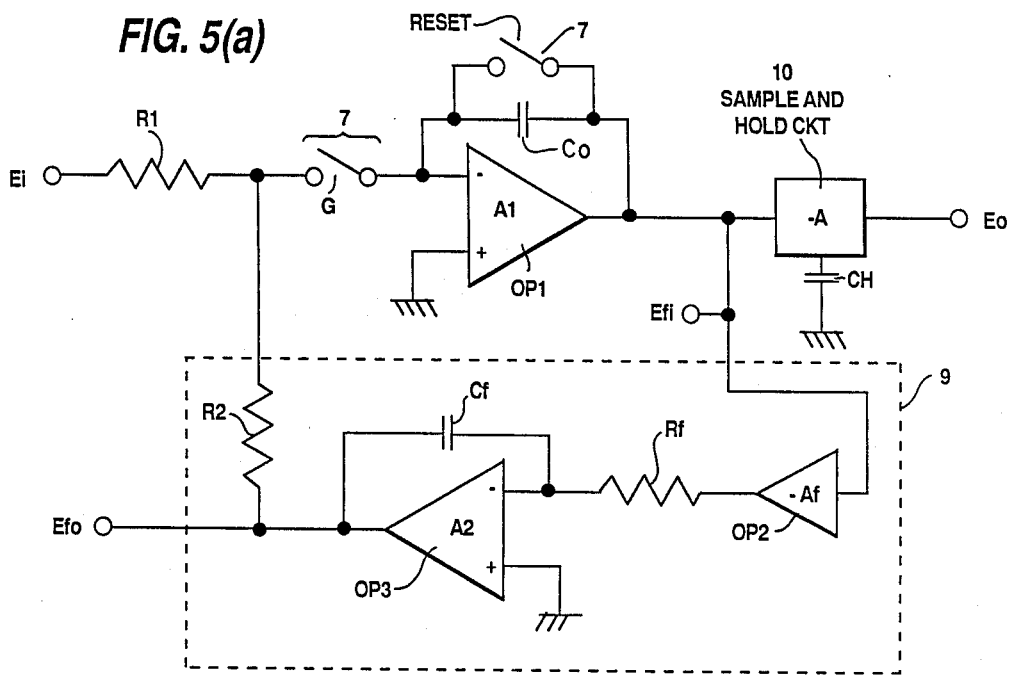
FIG. 5(a) is a practical circuit diagram in an embodiment of the essential parts of the flowmeter of FIG. 3.
Figure 5B:
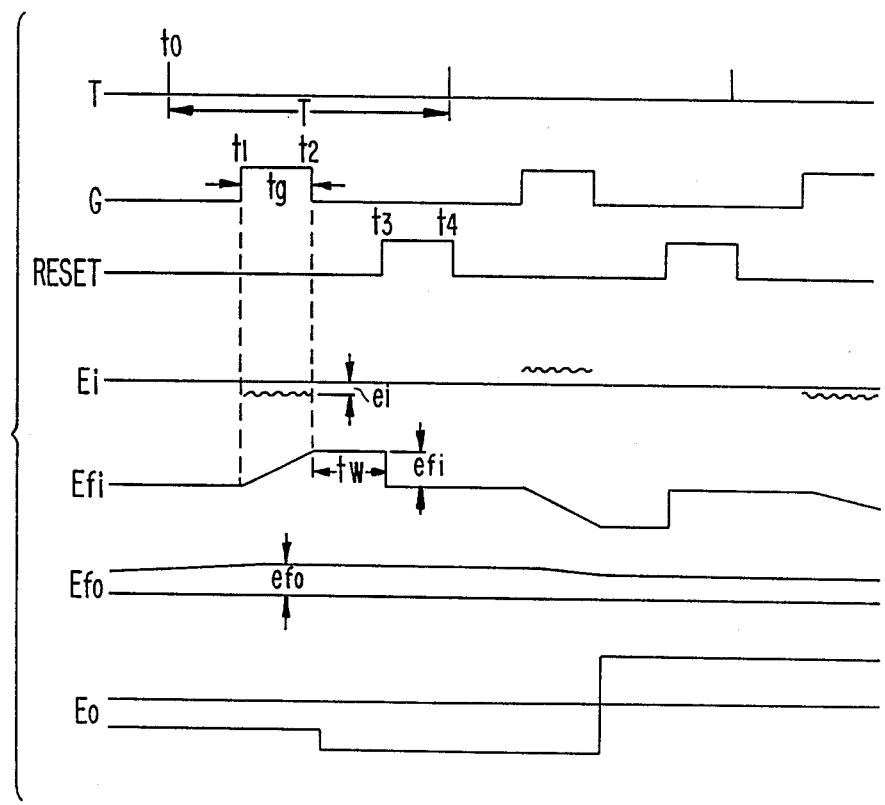
FIG. 5(b) is a time chart showing the operation of the circuit shown in FIG. 5(a)
Figure 5C:
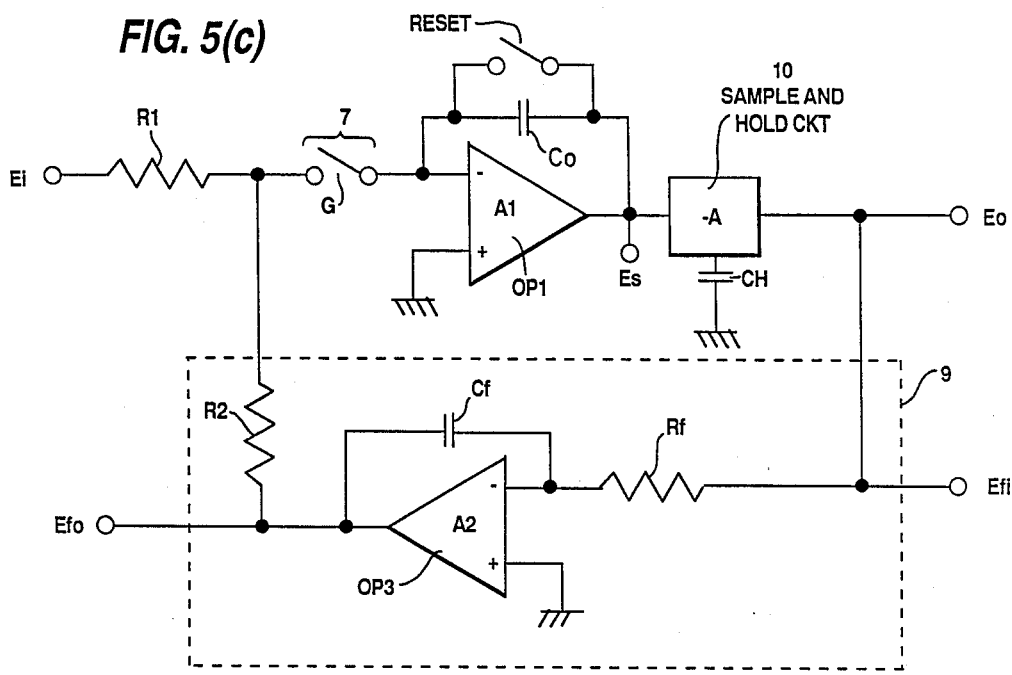
FIG. 5(c) is a practical circuit diagram in a different embodiment of the essential parts of the flowmeter of FIG. 3.

FIGS. 5(a) and 5(c) depict examples of practical circuits of the analog switch 7, integrating circuit 8, sample and hold circuit 10, and direct-current feedback circuit 9 as shown the embodiment of FIG. 4, and FIGS. 5(b) and (d) denote signal waveforms at each terminal of FIGS. 5(a) and (c). The circuit in FIG. 5(a) or FIG. 5(c) requires one system for the real part signal X and one system for the imaginary part signal Y, but only one system is shown in FIG. 5 the diagram. The circuits in (a) and (c) produce exactly the same effect. As a first embodiment, the operation of the circuit in FIG. 5(a) is explained below while referring to FIG. 5(b). The integrating circuit 8 in FIG. 4 is composed of, as shown in FIG. 5(a), an inverting amplifier $OP_1$ having a degree of amplification of $-A_1$, a resistance $R_1$, and capacitor $C_0$, and it has two input terminals, that is, $E_i$ to which the output of the phase detector 4 (see FIG. 4) is applied, and $E_{f0}$ to which a direct-current feedback voltage of direct-current feedback circuit 9 is applied, and the signals of both terminals are added immediately before the analog switch 7, and are integrated when the analog switch 7 is ON. The analog switch 7 is turned on in the period of $t_1$ to $t_2$ of gate signal G, and the signals are integrated for the time $t_g$, and a waveform as shown in the drawing is obtained at the input terminal (output of integrating circuit) $E_{fi}$ of the direct-current feedback circuit 9. The sample and hold circuit 10 has a gain of $-A$, and samples from $t_2$ when the integration is over to time $t_\omega$, and holds the sample after $t_3$. After holding, the integrating circuit, prior to the next transmission and reception, turns on the analog switch 7' to discharge $C_0$ for the period of $t_3$ to $t_4$ by means of RESET signal, and is reset. At the output terminal $E_0$ of the sample and hold circuit 10, a Doppler signal which has a discrete value in period T appears as shown in the diagram, and is supplied to high pass filter 11 (see FIG. 4). On the other hand, the direct-current feedback circuit 9 comprises a low pass filter by means of inverting amplifier $OP_3$, capacitor $C_f$ and resistance $R_f$, and direct-current and ultralow frequency components are extracted from the output signal of the integrating circuit $E_{fi}$, and are negatively fed back through resistance $R_2$. The inverting amplifier $OP_2$ has a gain of $-A_f$, and is intended to invert the phase. Therefore, the lower the frequency of the output of the integrating circuit, the more increases the feedback amount, and the integration result becomes smaller. Such input, output characteristics of the circuit may be obtained as follows.

$$I_{fi} = \frac{t_g}{C_0 R_1} I_i + \frac{t_g}{C_0 R_2} I_{f0} \quad (7)$$

$$I_{f0} = 1 \frac{1}{\omega C_f R_f} \frac{t_g K + t_\omega}{T} I_{fi} \quad (8)$$

Equation (7) refers to the relationship between the mean voltage $I_i$ of output of phase detector within gate time $t_g$ supplied to input terminal $E_i$, direct-current feedback voltage $e_{f0}$ supplied to input terminal $f_0$, and integrating circuit output $f_i$, and eq. (8) refers to the integrating circuit output $f_i$ and direct-current feedback voltage $e_{f0}$ supplied to the direct-current feedback circuit 9. In eq. (8), $\omega$ is the frequency of Doppler shift signal delivered to the integrating circuit, and $(t_g/K + t_\omega)/T$ is the duty cycle ratio of the Doppler shift signal existing discretely in every period T, and during the integration time of $t_1$ to $t_2$, its value is less than 1 to correct the duty cycle ratio in this duration because it is in the transient state until $f_i$. From eqs. (7), (8), the gain $A_v$ of circuit in FIG. 5(a) becomes as follows.

$$A_v = \frac{t_g}{C_0 R_1} \cdot \frac{1}{1 - j \frac{t_g}{\omega C_0 C_f R_2 R_f} \cdot \frac{t_g K + t_\omega}{T}} \quad (9)$$

Incidentally, the $-3$ dB low range cut-off frequency $f_c$ in eq. (9) is expressed as follows.

$$f_c = \frac{\sqrt{2}}{2\pi} \frac{t_g}{C_0 C_f R_2 R_f} \frac{t_g K + t_\omega}{T} \quad (10)$$

The value of $f_c$ should be selected at a frequency to sufficiently allow the passage of the Doppler shift signal due blood flow and to inhibit the Doppler shift signal due to internal movement of the body; in an ordinary ultrasonic pulse Doppler blood flowmeter with an ultrasonic pulse frequency of about 2 to 7 MHz, it should be properly selected to be in the range of 50 to 500 Hz.

Figure 5D:
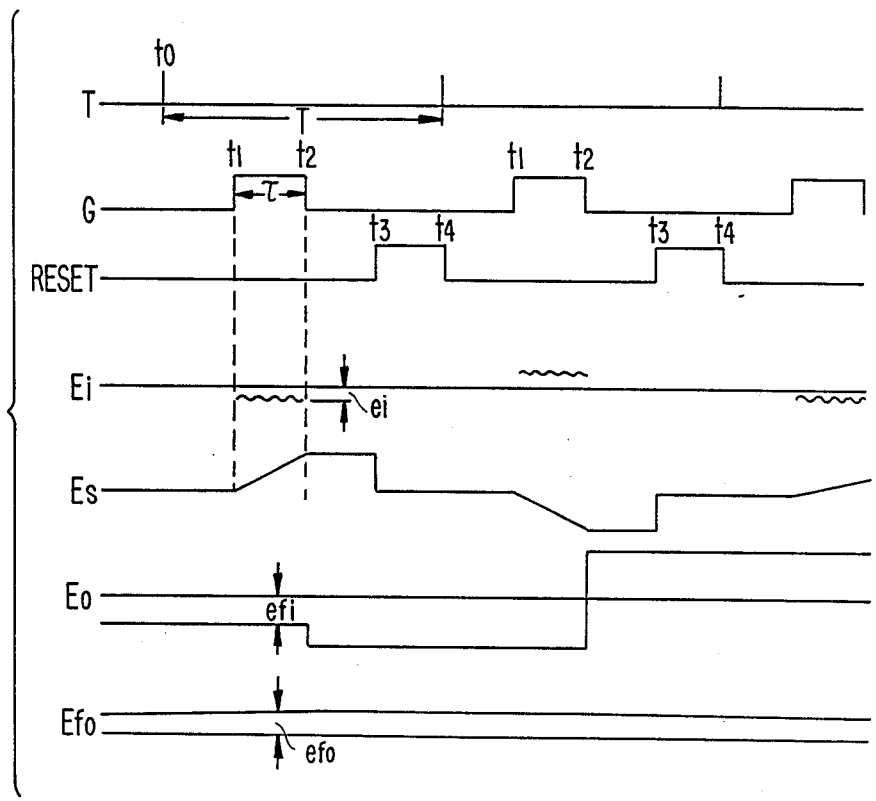
FIG. 5(d) is a time chart showing the operation of the circuit shown in FIG. 5(c)

As a second embodiment, the operation of the circuit in FIG. 5(c) is explained below while referring to FIG. 5(d). The principal construction and operation are same as in the first embodiment explained in FIG. 5(a), except that the output of the sample and hold circuit 10 is supplied to the integrating circuit, as compared with the first embodiment in FIG. 5(a) wherein the output of the integrating circuit is supplied to the input of the integrating circuit through the analog switch 7 by the direct-current feedback circuit 9. Incidentally, the inverting amplifier $OP_2$ used in the first embodiment is not needed because the sample and hold circuit 10 fulfills this function in this embodiment. The input and output characteristics of this circuit are obtained as follows.

$$I_0 = I_{fi} = A \left( \frac{t_g}{C_0 R_1} I_i + \frac{t_g}{C_0 R_2} I_{f0} \right) \quad (11)$$

$$I_{f0} = j \frac{1}{\omega C_f R_f} I_{fi} \quad (12)$$

Equations (11) and (12) correspond respectively to eqs. (7) and (8), from which the gain $A_v$ of the circuit in FIG. 5(c) is expressed as follows.

$$A_v = \frac{A t_g}{C_0 R_1} - \frac{1}{1 - j \frac{A t_g}{\omega C_0 C_f R_2 R_f}} \quad (13)$$

Meanwhile, the $-3$ dB low range cut-off frequency $f_c$ in eq. (13) is expressed in the following equation.

$$f_c = \frac{\sqrt{2}}{2\pi} \frac{A t_g}{C_0 C_f R_2 R_f} \quad (14)$$

Figure 5E:
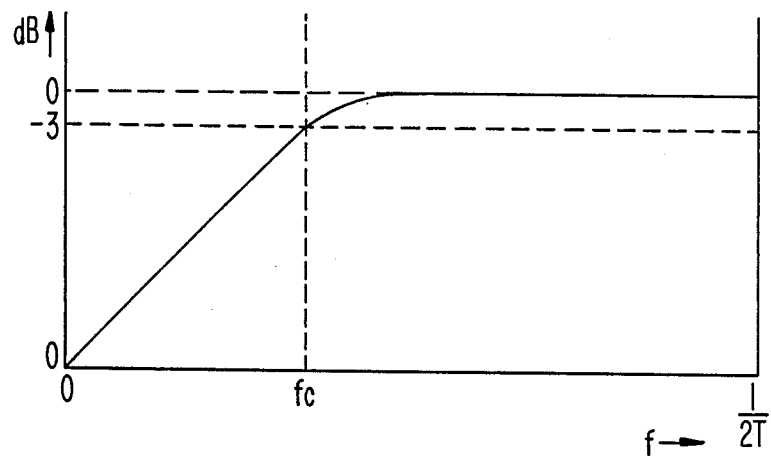
FIG. 5(e) is a diagram showing the frequency characteristics of the circuits shown in FIGS. 5(a) and 5(c)

The value of $f_c$ is determined in the same fashion as in FIG. 5(a), and FIG. 5(e) illustrated the frequency characteristics of the circuits in FIG. 5(a) and FIG. 5(c). As shown in the diagram, only the effects of the body tissues can be eliminated, and a frequency $f_c$ free from adverse effects on the detection of Doppler shift from the blood flow can be selected, so that only the alternating-current components which are Doppler shift signals can be delivered to the subsequent circuits without integrating the direct-current components. Thus, the Doppler shift signals appearing at the orthogonal signals X and Y, being rid of direct-current components, are completely free from influences if signals from the body tissues are received simultaneously in the echo signals.

Figure 6:
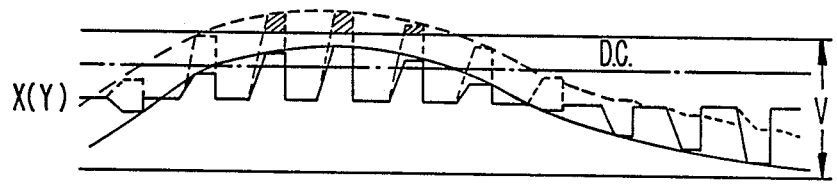
FIG. 6 is a diagram used to compare the integrated waveforms of this invention and the prior art.

FIG. 6 shows the output waveforms of the integrating circuit 8 of this embodiment and the prior art. The solid line refers to this invention, and the broken line denotes the prior art, and the shaded area is the portion of the waveform being cut off by saturation. As shown in the diagram, by executing this invention, the amplitude limit is expanded, and there occurs no effect of direct-current voltage, so that a very fine blood vessel can be measured, without saturating the integrating circuit 8, and that the amplitude of the Doppler shift signal can make use of the amplitude limit V to the maximum extent.

As explained above, by the ultrasonic Doppler blood flowmeter of this invention, since the direct-current component or ultralow frequency component of Doppler shift signal obtained from the integrating circuit is negatively fed back by the direct-current feedback circuit, if an echo signal without a time change from the body tissue is captured at the same time as an echo signal from the blood flow, in this simple circuit composition, the frequency of the blood flow only can be analyzed, and no display other than that of the blood flow appears on the blood flow pattern on the display unit, so that accurate information about the direction of the blood flow can be obtained.

FIG. 7 is a block circuit diagram of an ultrasonic Doppler blood flowmeter in another embodiment of this invention. This embodiment involves a feedback gain control circuit 14 which controls the feedback gain of the direct-current feedback circuit 9 in the composition shown in FIG. 4, depending on the gate width information set in the gate signal generating circuit 6. The other structure and operation are the same as that of FIG. 4.

Figure 8A:
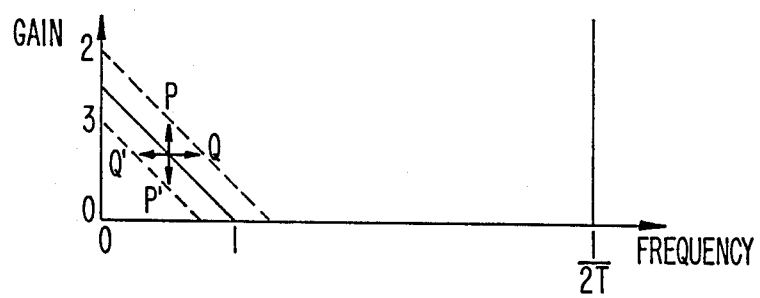
FIGS. 8(a) and 8(b) the shows frequency characteristics of direct-current feedback circuit and integrating circuit of the flowmeter of FIG. 7.
Figure 8B:
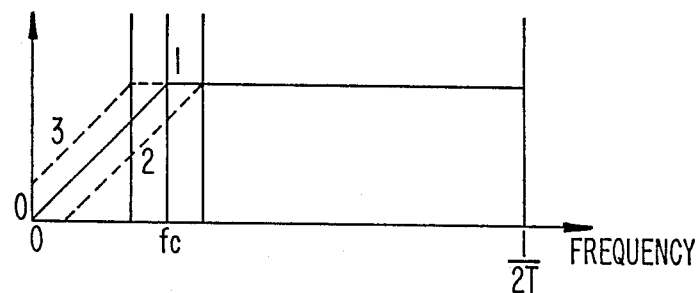

The high pass filter of integrating circuit 8 has the characteristic as shown in FIG. 8(b), but by expanding the gate time $t_G$, the duration of the application of the feedback signal to the integrating circuit 8 is extended, and the same effect as when the gain of the direct-current feedback circuit 9 is increased is produced, which causes to shift the characteristic 1 in FIG. 8(a) toward the direction P to become characteristic 2, which results in the characteristic 2 of the integrating circuit FIG. 8(b). To keep the frequency characteristic of the integrating circuit 8 at curve 1, as the gate width expands, the gain of the direct-current feedback circuit 9 is lowered to correct in the direction of P'. Or, by lowering the cut-off frequency of the direct-current feedback circuit 9 and correcting the characteristic in the direction of Q', the increase of the gain of direct-current feedback circuit 9 due to the expansion of the gate width is canceled, so that the cut-off frequency $f_c$ may be kept constant. When the gate width is shortened, similarly, it is enough to correct the characteristic of the direct-current feedback circuit 9 in the direction of P or Q. The feedback gain control circuit 14 is responsible for such correction, and it controls the degree of amplification $A_f$ of the entire direct-current feedback circuit 9, corresponding to the set gate width, that is, the time $t_G$ while analog switch 7 is ON, by determining the amplification according to the following equation.

$$A_f \propto 1/t_G \quad (15)$$

Figure 9A:
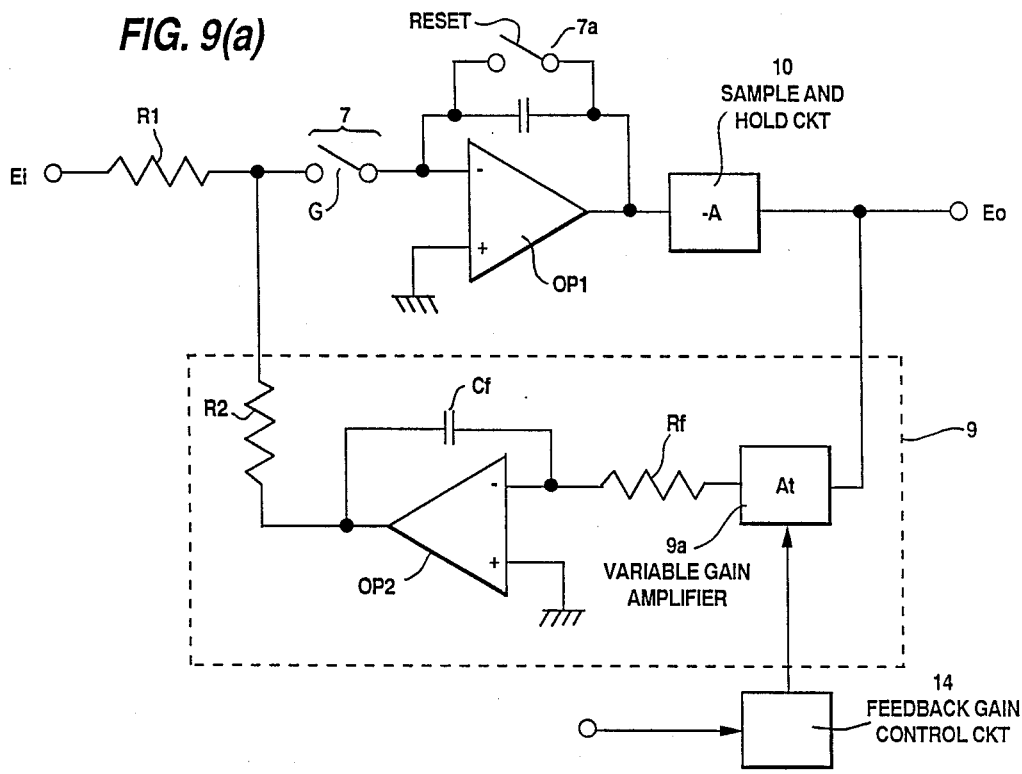
FIGS. 9(a) and 9(b) are practical circuit diagrams showing the integrating circuit, direct-current feedback circuit, and feedback gain control circuit in a further different embodiment of the ultrasonic Doppler blood flowmeter of this invention.
Figure 9B:
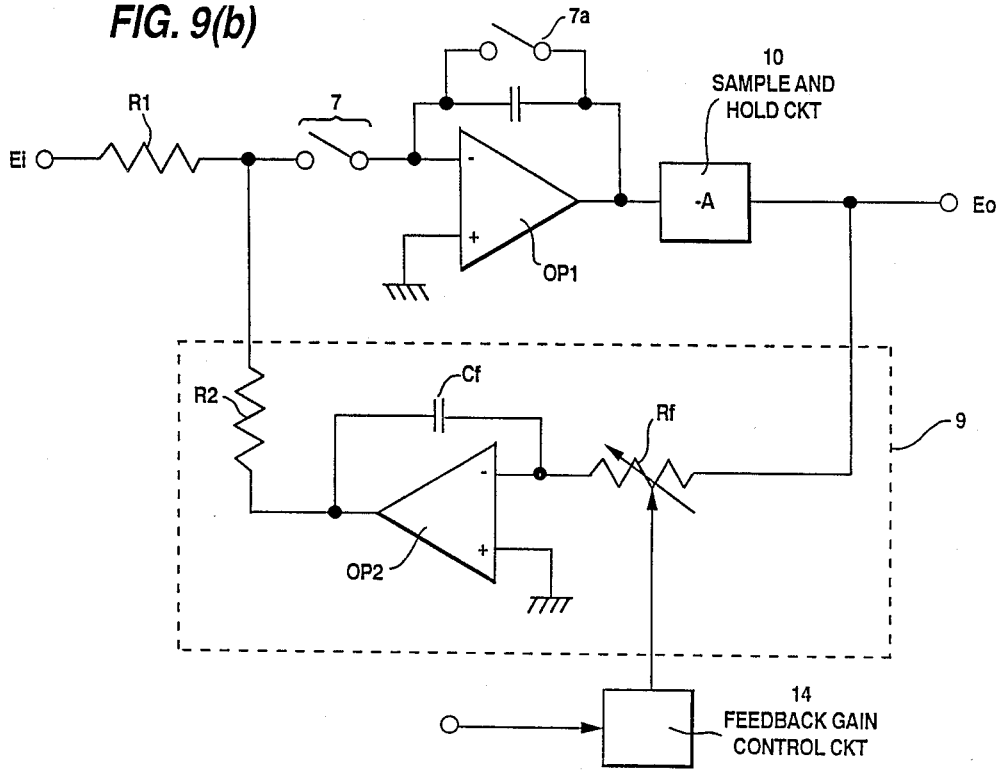

FIGS. 9(a) and (b) relate to an embodiment of circuit structure for correcting the above-mentioned shut-off frequency, in which FIG. 9(a) shows a circuit which is designed to correct the gain of the direct-current feedback circuit 9 by means of a variable gain amplifier 9a according to eq. (15), while FIG. 9(b) shows a circuit which changes the cut-off frequency of the direct-current feedback circuit 9, by changing the resistance Rf. In FIG. 8(a), when the gate width is extended, the characteristic 1 moves toward the direction of P, and it is corrected by moving to the direction of Q', by lowering the cut-off frequency. Besides, it is also possible to correct by varying the capacitor Cf or resistance $R_2$.

Figure 10A:
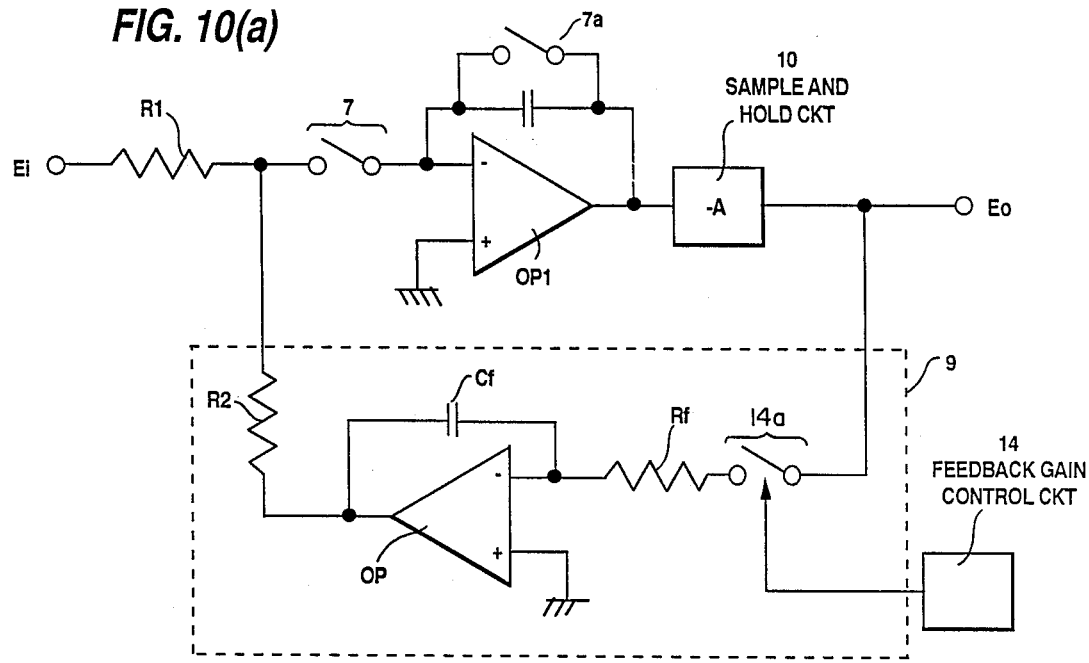
FIG. 10(a) is a practical circuit diagram showing the integrating circuit, direct-current feedback circuit, and feedback gain control circuit in a still further embodiment of the ultrasonic Doppler blood flowmeter of this invention.
Figure 10B:
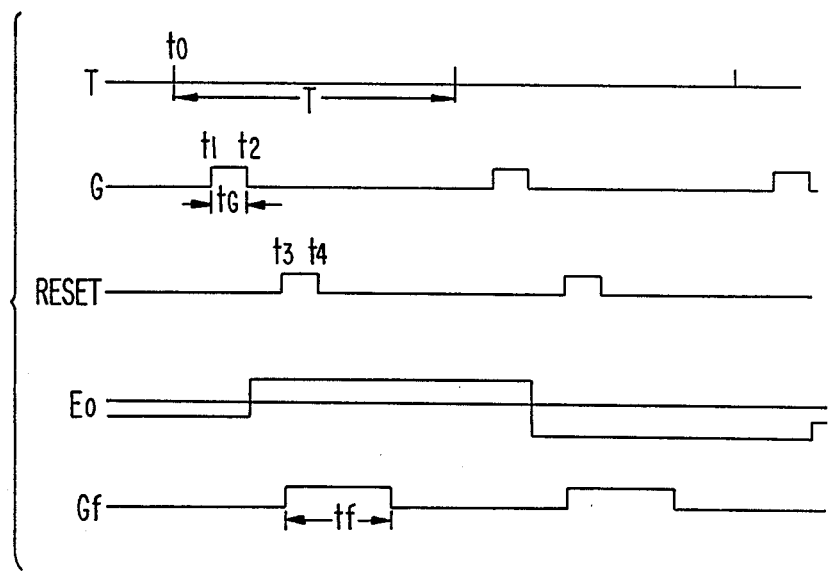
FIG. 10(b) is an operation timing chart of the circuit of FIG. 10(a).

FIG. 10(a) refers to a further different embodiment, in which 14a is an analog switch used to turn on and off the Doppler shift signal fed into the direct-current feedback circuit 9; the feedback gain controls circuit 14 control the time width $t_f$ in which the analog switch 14a is ON by the gate width $t_G$. FIG. 10(b) shows the control timing of the analog switch 14a. Its operation is described below. As in the preceding embodiments, the Doppler shift signal appearing at output $E_0$ has its ultralow frequency components in the direct-current feedback signal 9, and is fed back in reverse phase, but at the input of direct-current feedback circuit, the analog switch 14a is connected, and by controlling the duty ratio $t_f/T$ of the gain control signal $G_f$ generated depending on the gate width $t_G$ by the feedback gain control circuit 14, the entire gain of the direct-current feedback circuit 9 is varied and corrected.

Thus, by the ultrasonic Doppler blood flowmeter of these embodiments herein, by applying a gain depending on the gate width to the direct-current feedback circuit by the feedback gain control circuit, the cut-off frequency of the integrating circuit may be kept constant regardless of the gate width, and the measurement of the rate of blood flow being free from the effects of the Doppler shift signal from the body tissues can be effected in the same conditions regardless of the gate width, and its clinical effect is extremely notable.

What is claimed is:

1. An ultrasonic Doppler blood flowmeter adapted for measuring the flow of blood through a body of a subject, said flowmeter comprising, at least, an ultrasonic transmission means for transmitting ultrasonic pulses into the body of a subject; an ultrasonic reception means for receiving echo signals reflected within the body; a drive circuit means for generating ultrasonic pulses to be transmitted by said ultrasonic transmission means; a transmission timing signal circuit means for generating timing signals used to generate ultrasonic pulses by means of said drive circuit means; a phase detecting means for detecting the amplitude and phase of each of said echo signals obtained by said ultrasonic reception means; a reference signal generation circuit means for generating a reference signal serving as the reference for the frequency and phase of a transmission signal of said drive circuit means and a reference signal for frequency and phase when detecting the phase of each of said echo signal; a gate signal generating circuit means operatively connected to said transmission timing signal circuit means and to said reference signal generating circuit means for generating a gate signal of variable period at a time corresponding to an echo signal from a desired position; a control means for controlling the transmission therethrough of the phase signal detected by said phase detecting means in response to said gate signal; an integrating circuit means for obtaining a Doppler shift signal by integrating the phase signal transmitted through said control means; a sample and hold circuit means for temporarily holding the integrated result obtained by said integrating circuit means; a variable gain feedback circuit means for negatively feeding back a direct-current component of an ultra-low frequency component of the Doppler shift signal obtained by said integrating circuit means or held by said sample and hold circuit into said integrating circuit means; and a feedback gain control circuit means for controlling the gain of said feedback circuit in proportion to the period of said ultrasonic pulses or in inverse proportion to the time width of said gate signal generated by said gate signal circuit means.

2. An ultrasonic Doppler blood flowmeter as recited in claim 1, wherein said feedback circuit means is consisting of a low pass filter using an integrating circuit means and a gain variable amplifier for controlling the gain thereof.

3. An ultrasonic Doppler blood flowmeter as recited in claim 1, wherein said feedback circuit means is consisting of a low pass filter using an integrating circuit means and a time constant control circuit means for controlling the time constant of said integrating circuit means.

4. An ultrasonic Doppler blood flowmeter as recited in claim 1, wherein said feedback circuit means is consisting of a low pass filter using an integrating circuit means and a chopper circuit means which turns the input of said integrating circuit means on and off.

5. An ultrasonic Doppler blood flowmeter as recited in claim 1, wherein said feedback circuit means is connected to said control means such that said feedback signal from the feedback circuit means is fed back to the input terminal of said control means.

6. An ultrasonic Doppler blood flowmeter as recited in claim 1, wherein said ultrasonic transmission means and said ultrasonic reception means together comprise one ultrasonic probe.

7. An ultrasonic Doppler blood flowmeter as recited in claim 1, wherein said control means comprises an analog switch.

* * * * *